United States Patent [19]
Berall

[11] Patent Number: 5,827,178
[45] Date of Patent: Oct. 27, 1998

[54] LARYNGOSCOPE FOR USE IN TRACHEA INTUBATION

[76] Inventor: Jonathan Berall, 173 Columbia Heights, Brooklyn, N.Y. 11201

[21] Appl. No.: 778,079

[22] Filed: Jan. 2, 1997

[51] Int. Cl.⁶ .......................................... A61B 1/26
[52] U.S. Cl. ............................................ 600/185; 600/188
[58] Field of Search ..................... 600/185, 188, 600/199, 194, 196, 237, 245

[56] References Cited

U.S. PATENT DOCUMENTS

| | | | |
|---|---|---|---|
| 4,592,343 | 6/1986 | Upsher | 600/188 |
| 5,263,472 | 11/1993 | Ough | 600/188 |
| 5,363,838 | 11/1994 | George | 600/185 |

*Primary Examiner*—Michael Powell Buiz
*Assistant Examiner*—Kevin Troung
*Attorney, Agent, or Firm*—Charles E. Baxley, Esq.

[57] ABSTRACT

A laryngoscope, for use in intubating a patient's trachea, especially in emergency situations. The laryngoscope has a camera mounted in the vicinity of a distal end of its blade to observe the patient's trachea opening and other oral internal structures in a visual field. The camera is connected, typically via a fiberoptic cable, to a lightweight portable television screen, preferably mounted on the laryngoscope handle, for displaying the visual field to the a Professional Intubator so as to enable him or her to observe continuously the trachea opening and other oral internal structures as he or she manipulates the intubating instrument. The laryngoscope with the camera and screen thereon preferably is held in one of the Professional Intubator's hands to lift and move aside the patient's tongue steadily and constantly. The other hand of the Professional Intubator then is free to manipulate the intubating instrument. Mounting the camera and the screen on the laryngoscope, which remains quite steady, provides the Professional Intubator with a continuous steady display of the trachea opening and other oral internal structures on the screen while the intubator also sees directly down the patient's mouth.

16 Claims, 4 Drawing Sheets

LARYNGOSCOPE FOR USE IN TRACHEA INTUBATION

BACKGROUND OF THE INVENTION

1. Field of Invention

This invention relates generally to fiberoptic scopes and more particularly to a laryngoscope having such a scope with an associated lightweight portable screen. Said laryngoscope is particularly useful in a procedure for intubating a patient's trachea, especially in emergency situations.

2. Relevant Prior Art

A fiberoptic intubating instrument having thereon a scope with a camera and an associated lightweight portable screen was disclosed by Dr. Gordon George in U.S. Pat. No. 5,363,838 which issued on Nov. 15, 1994. Dr. George had also authored U.S. Pat. No. 4,742,819 which had issued on May 10, 1988 wherein he had likewise disclosed a prior version of an intubating instrument having thereon a scope with a camera and a screen associated therewith.

U.S. Pat. No. 4,086,919 to Bullard disclosed a laryngoscope having a single eyepiece attached to the laryngoscope blade. The eyepiece is illuminated by a fiberoptic system. If the person performing an intubation procedure, such as a physician, nurse, paramedic, or an emergency medical technician (each hereinafter sometimes referred to as a "Professional Intubator") looks through the Bullard scope and has to remove his eyes from the eyepiece to make an external assessment of the airway of the patient, a critical lag in time occurs before the Professional Intubator can re-focus on the internal images seen through the eyepiece. The critical lapse of time caused by the process of focusing and refocusing can affect timely placement of the endotracheal tube and may even cause the Professional Intubator to misinterpret certain landmarks, hindering correct placement of the endotracheal tube. Most importantly, movement of the Professional Intubator's body and head, down to and away from the eyepiece, can lead to erroneous placement of the endotracheal tube in a structure other than the patient's airway. Such erroneous placement can result in death or serious brain damage to the patient, so importance of correct endotracheal tube placement cannot be overemphasized.

DISCUSSION OF PROCEDURE

In performing an intubating procedure, the Professional Intubator holds a laryngoscope in one hand for lifting the patient's tongue to one side to expose the patient's trachea opening and the Professional Intubator simultaneously operates an intubating instrument in his or her other hand for inserting a tube into the patient's trachea. In performing the procedure the Professional Intubator must move and manipulate the intubating instrument which necessarily moves and disturbs a scope or camera if it were mounted thereon. Thus the movement would disturb and disrupt display of the patient's oral internal structures that would appear on the screen of Dr. George. But, in contrast, the Professional Intubator's hand holding the laryngoscope to keep the patient's tongue out of the intubator's line of sight, stays steady and constant. So Applicant here teaches to mount the scope or camera in the vicinity of the distal end of the blade of the laryngoscope, instead of on the intubating instrument, whereby display of the patient's oral internal structures remains quite steady while the Professional Intubator's other hand is free to move and manipulate the intubating instrument in inserting the tube it into the patient's trachea.

It is necessary frequently in medical procedures to insert an tube into the trachea of a patient for ventilation, oxygenation and/or airway protection. Intubation is often difficult and can give rise to complications. It is frequently performed in critical and life-threatening situations on severely compromised patients in awkward emergency sites. Even a short period of oxygen deprivation can result in death or severe brain damage of the patient. A common ingredient for failure when attempting intubation is that when the Professional Intubator's view of the patient's tracheal opening becomes obstructed. That situation of obstructed view is called blind intubation. The most common cause of blind intubation is that the tongue slips over the laryngoscope blade and obstructs the Professional Intubator's view of the tracheal opening. The tongue being large, floppy, moist and slippery, easily does slip over the laryngoscope blade and down into the line of vision between the Professional Intubator and the tracheal opening he or she is trying to view. Additionally, sometimes neck type and abnormalities of the patient's pharynx, such as abscesses, cancers and even congenital abnormalities can result in an inability to see directly the tracheal opening, thus resulting in failure of intubation.

In many patients establishment of the airway may be a formidable task due to morphologic anomalies such as a large tongue, excessive pharyngeal or laryngeal soft tissue or tracheal displacement, as well as physiologic events such as laryngospasm, regurgitation of gastric materials, blood or foreign bodies. The morphologic anomalies already mentioned make it difficult to visualize the posterior pharyngeal area and larynx. The present invention helps minimize risks brought on by such anomalies.

In terms of neck type, short necks cannot extend fully whereby the Professional Intubator's direct line of vision (180° angle) is not achieved between the Professional Intubator's eye and the tracheal opening and there is blind intubation. Blind intubation, unfortunately is rarely successful.

The laryngoscope blade is easily passed, conventionally using the Professional Intubator's left hand, behind the base of the tongue and into the pharynx. The instrument for inserting the endotracheal tube is also passed, conventionally using the Professional Intubator's right hand, behind the base of the tongue and into the pharynx. The laryngoscope with its blade (once positioned) is held, by the Professional Intubator's left hand, in a steady and firm minimally changing position. The instrument for inserting the endotracheal tube is moved in varying positions by the Professional Intubator's right hand to enter the tracheal opening. The laryngoscope according to the present invention is a modification of current state of the art laryngoscopes such that a scope or camera is mounted on its distal end, preferably at or in the vicinity of the far tip of the laryngoscope blade, preferably spaced slightly rearwardly therefrom for reasons which will appear more fully herein. The camera is operatively connected to a screen arranged for viewing by the Professional Intubator. The screen can be attached (preferably pivotally) to the handle of the laryngoscope above the blade, so that the Professional Intubator's direct view into the mouth and simultaneous view of the screen can be achieved with no head movement by the Professional Intubator and minimal change in his or her line of vision— that is to say, eye movement. When the laryngoscope is positioned it is held in a substantially stable condition so that the scope or camera is steady and the screen displays a stable picture whereby insertion of the intubating instrument into the patient's trachea, and the entire endotracheal intubating procedure are greatly facilitated.

Once the laryngoscope blade, scope or camera and screen are steadied, the endotracheal tube is passed easily and conveniently into the posterior pharynx. As it passes the cameras eye the endotracheal tube appears on the screen so then the Professional Intubator has the tube and the tracheal opening both in simultaneous view on the screen which preferably is positioned very close to his or her direct line of sight. The Professional Intubator then has the endotracheal tube distal end and the tracheal opening on the screen and bringing the two together becomes a simplified and relatively relaxed procedure. Further the Professional Intubator can also look right at the patient's teacheal opening.

Fiberoptic scopes have been used in association with screens, video systems, tapes and discs in other areas of medicine as well. Scopes used for arthroscopy with screens set on a monitor off to one side of an operating room table are just one example. Another example is use of a fiberoptic scope in performance of laparoscopic cholecystectomy. The screen, and with it the monitoring images is removed from the direction of the operation. To use such fiberoptic scopes and devices for intubation of a trachea, especially in patients who present airways that are complicated, is not an optimal answer for emergency intubation. If such a scope is mounted on the instrument for inserting the endotracheal tube to view the patient's airway structures, as the distal end of the instrument and endotracheal tube go out of sight the Professional Intubator has to turn his or her head and/or body in a significant manner to view the associated screen. If mouth and throat structures are seen that are not easily identifiable, the Professional Intubator then has to turn his or her head and/or body back to the direct viewing of the airway to see just where the endotracheal tube is placed, and make an adjustment of the endotracheal tube in the airway in relation to anatomic structures that are present. Then as the endotracheal tube goes out of sight again, the Professional Intubator has to turn his or her head and body off to the side to again look at the screen. Because according to prior art arrangements, a Professional Intubator cannot simultaneously view the airway directly and indirectly through the screen, confusion, lack of orientation of the endotracheal tube and its proper position in the airway can result, potentially leading to failure in an intubating process.

The invention set forth in Dr. George's U.S. Pat. No. 5,363,838 entitled "Fiberoptic Intubating Scope with Camera and Lightweight Portable Screen and Method of Using Same" comes close to achieving optimum conditions to assuring quick, accurate and easy placement of the endotracheal tube in a patient's trachea. The present invention goes further by enabling the Professional Intubator simultaneously to see the patient's airway directly and indirectly as a steady picture on screen. The present invention likewise enables the Professional Intubator to move his or her eyes only minimally during the intubating procedure so that he or she does not have to turn his or her head or body to visualize indirectly the airway, as would be required with a screen that were set off to the side and not close to the direct line of vision of the task at hand.

Normally a Professional Intubator is either right-handed or left-handed, which is to say he or she has a dominant hand and a less-dominant hand. Normally the Professional Intubator would be inclined to use his or her less-dominant hand to hold the laryngoscope, because the less-dominant hand is sufficient for lifting and moving to one side the patient's tongue steadily and constantly during the intubation procedure. Traditionally Professional Intubators have been trained to hold a laryngoscope in his or her left hand, but that tradition is not carved in stone. Because the less-dominant hand and the blade of the laryngoscope are easily held steady, the field of view which the scope or camera observes likewise is quite steady. The dominant hand of the Professional Intubator, with superior agility, then is available to manipulate the intubating instrument without bouncing disturbing or disrupting the display on the screen.

SUMMARY OF THE INVENTION

A primary object of the present invention is to provide a laryngoscope for use with an intubating instrument in a procedure for intubating a trachea of a patient, especially a patient whose pharynx, larynx and trachea are not easily visualized.

A further object is to provide such a laryngoscope which is user-friendly to the Professional Intubator.

A further object is to provide a laryngoscope with a scope or camera and display screen which do not require the Professional Intubator to turn his or her head away from direct visualization of the operating field during the intubation procedure.

A further object of the invention is to provide such a laryngoscope which can be set up quickly and easily.

A further object of this invention is to provide such a laryngoscope which is self-contained, lightweight and portable.

A further object of the invention is to provide such a laryngoscope which allows the Professional Intubator to see more superficial structures of the oral pharynx by direct vision and simultaneously to see the deeper structures of the larynx and trachea indirectly through the screen arrangeable close to his or her direct line of sight into the operating field.

A further object of the invention is to enable the Professional Intubator to lift and move aside the patient's tongue and position the camera steadily and constantly during the intubation procedure with his or her less-dominant hand, thereby allowing the Professional Intubator to manipulate the incubating instrument with his or her dominant hand without jostling the scope or camera.

These and other objects and advantages will be apparent to those skilled in the art in light of the following disclosure, claims and accompanying drawings.

BRIEF DESCRIPTION OF THE DRAWINGS

Throughout the drawings the same reference characters indicate the same or similar parts.

DESCRIPTION OF PREFERRED EMBODIMENT

Figure 1:
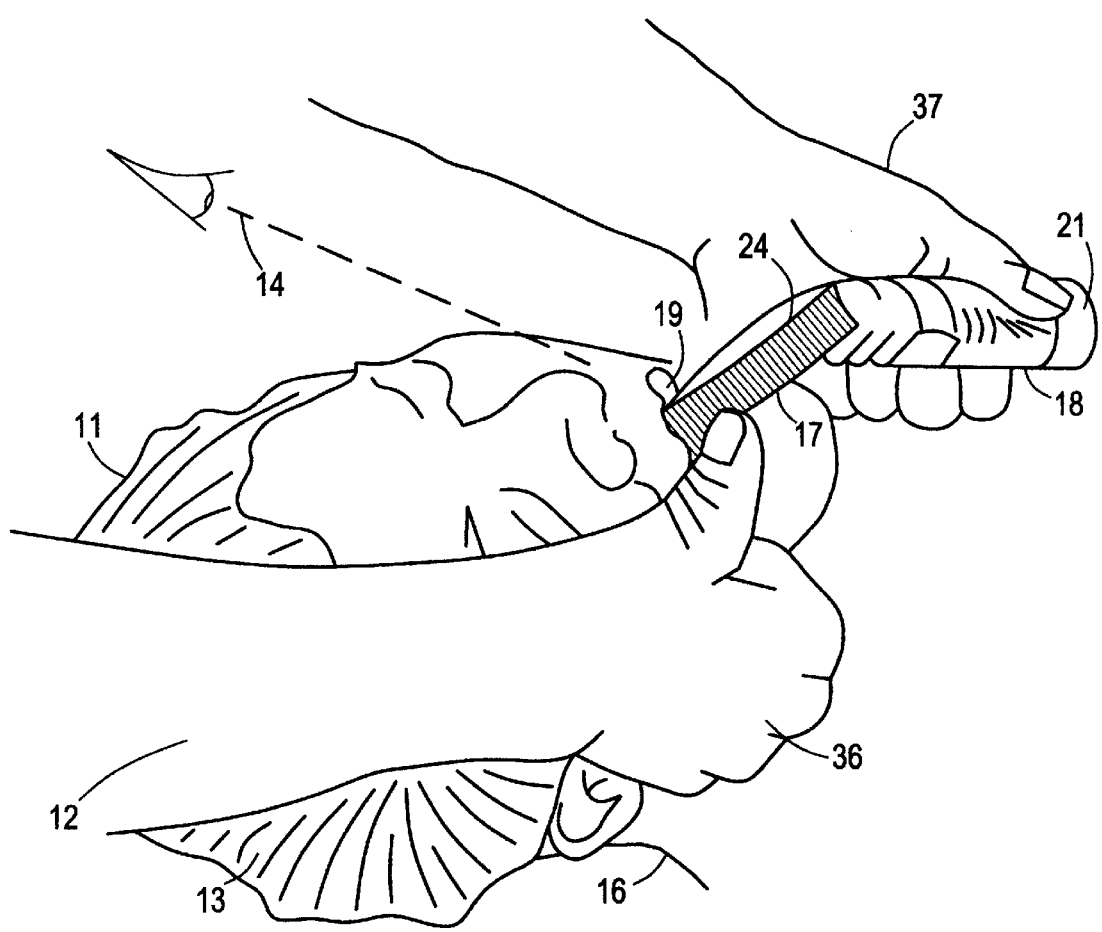
FIG. 1 is an illustration of the patient laying flat on a suitable platform with his or her neck drawn back and the Professional Intubator positioned behind the patient's head. The Professional Intubator may be a physician, nurse, paramedic or an emergency medical technician. The Professional Intubator is using his or her left hand to insert the blade of the laryngoscope into the patient's mouth while drawing the patient's neck back.

Referring to FIG. 1 patient 11 is arranged on a platform (not shown) with a Professional Intubator 12 taking a position behind the patient's head 13 so that the Professional Intubator can have a direct line of sight 14 directly down the patient's throat 15. A neck 16 of the patient 11 is drawn rearwardly to enable the Professional Intubator 12 to see more clearly down the patient's throat. With his or her left hand the Professional Intubator 12 inserts a blade 17 of a laryngoscope 18 into the patient's mouth 19 and gently draws and rotates the handle 21 of the laryngoscope 18 toward the Professional Intubator 12 and lifts the patient's tongue 22 moving it to one side whereby the Professional Intubator 12 now is afforded a direct line of sight through the patient's mouth down the patient's throat 15 to his or her pharynx and the area of the patient's trachea opening 23.

Figure 2:
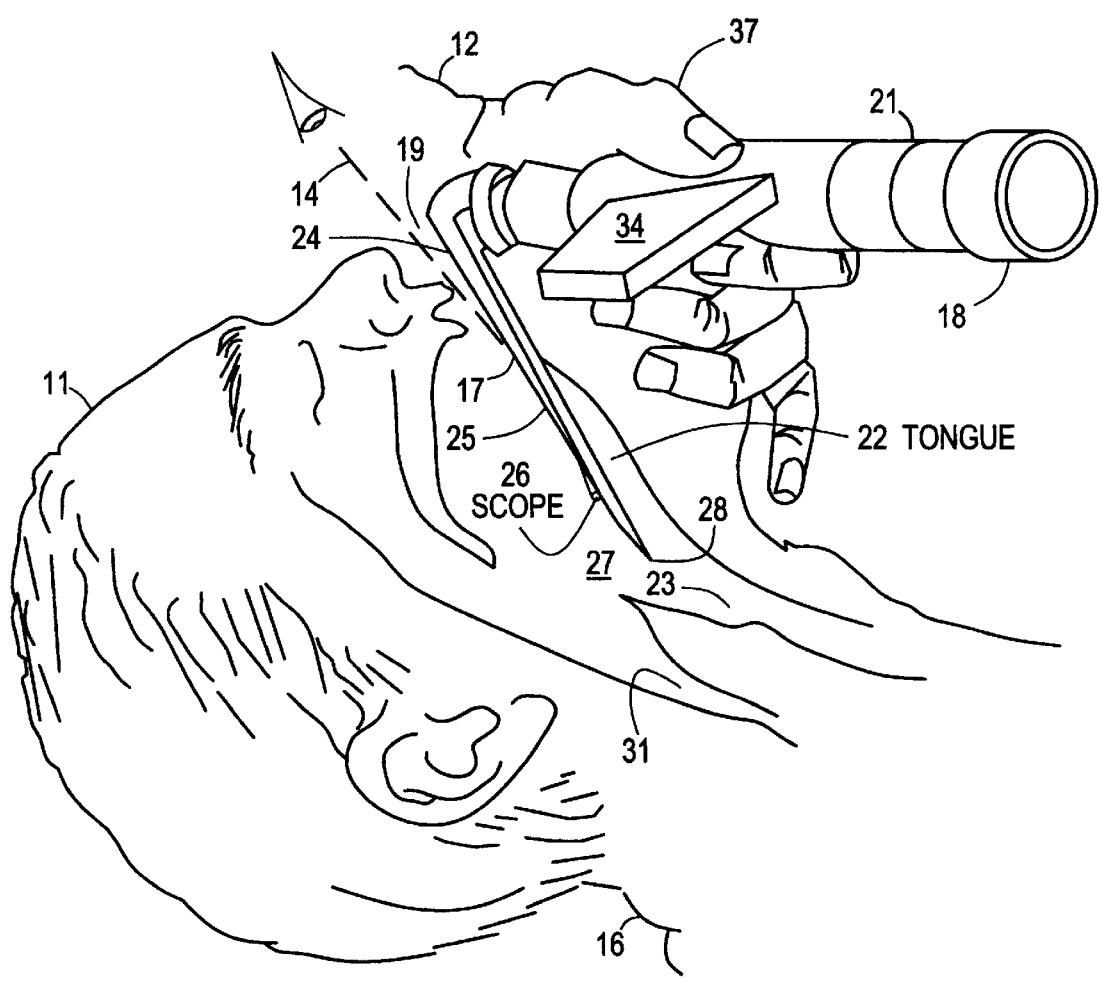
FIG. 2 illustrates the laryngoscope in its functioning position, to offer the Professional Intubator a direct line of vision to the patient's trachea opening and other oral internal structures near thereto.

Referring to FIG. 2, the laryngoscope 18 includes the handle 21 with the blade 17. The blade 17 has a proximal end 24 and a distal end 25. A scope or camera 26 is mounted on the blade 17 in the vicinity of the distal end 25 for observing a visual field 27 which includes mouth and throat internal structures associated with the trachea opening 23. The camera 26 could be at the tip 28 of the blade 17, but that would be disadvantageous if the tip 17 were to set involved in one soft tissue obstruction or another. Under ideal circumstances a highly skilled Professional Intubator 12 can distinguish and manipulate various structures, such as the patient's epiglottis. In emergency circumstances, taking into account various levels of skill of Professional Intubators, the crucial objective is to afford reliable placement of the intubating instrument into the trachea opening 23, rather than have it pass into the patient's esophagus 31. So the scope or camera 26 is located strategically best to see the trachea opening 23 whereby the intubating instrument can be inserted reliably therein.

Figure 3:
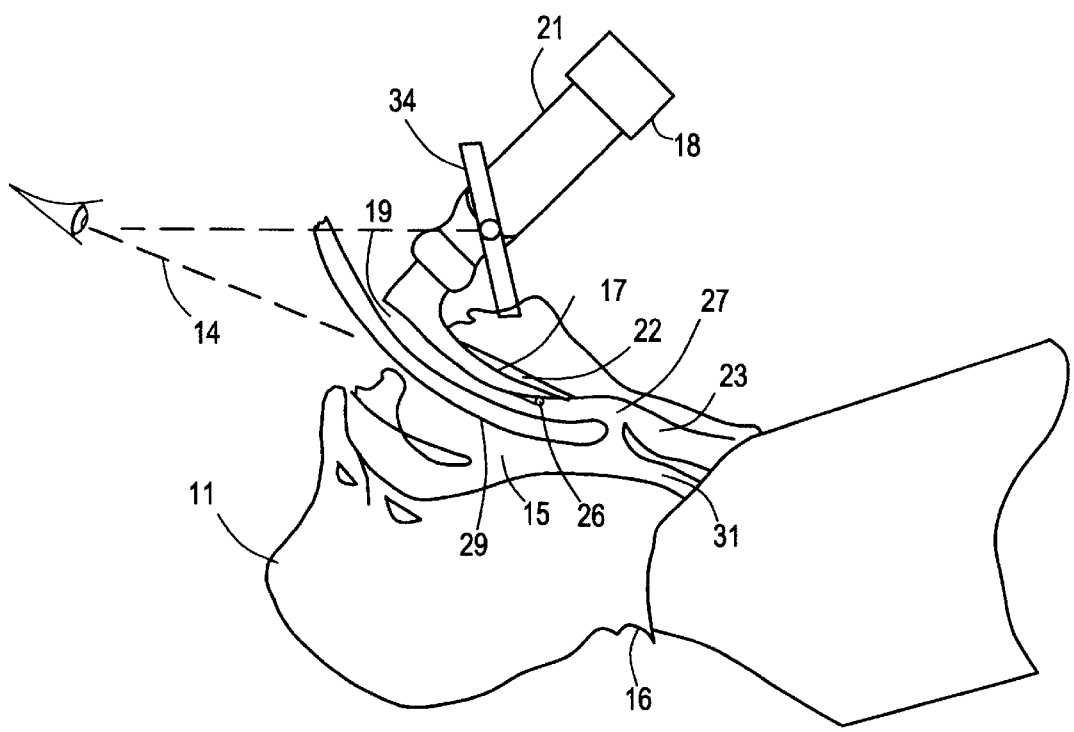
FIG. 3 illustrates insertion of the intubating instrument into the trachea of the patient.
Figure 4:
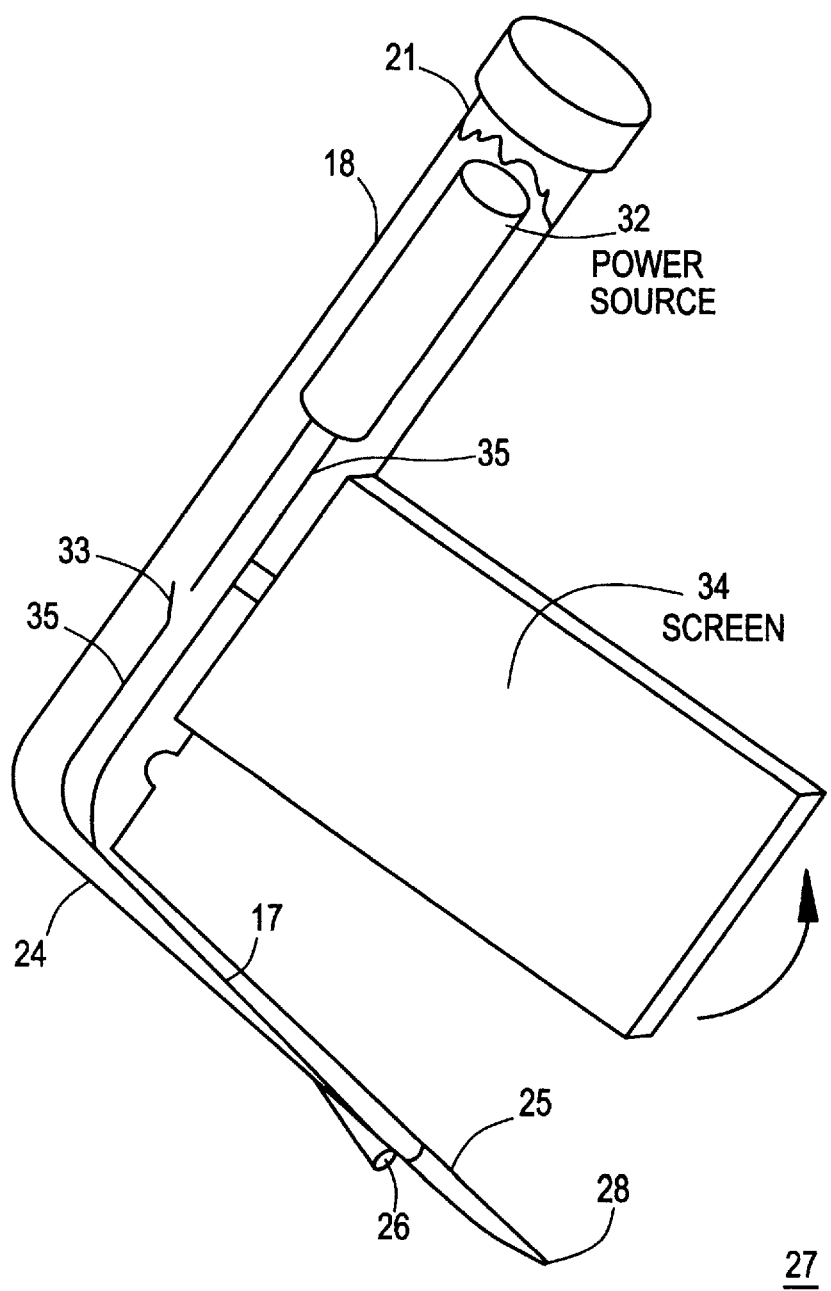
FIG. 4 is a circuit showing the operative relationships of the scope or camera means, the power supply means and the display means.

The camera 26 (shown best in FIG. 4) is powered by a battery 32 preferably in the handle 21 and a suitable on-off switch 33 is provided. The display means is shown as a television screen 34 mounted on the handle 21 and may be arranged to swivel as indicated in FIGS. 2 and 3. It is desirable to position the screen 34 as close to the Professional Intubator's 12 line of sight 14 as possible. The battery 32 can be recharged in the usual way. Alternately the laryngoscope 18 could be powered via a hard wire or plug-in connection to another power source.

The laryngoscope 18 preferably is made of lightweight hard plastic and the blade 17 is detachable for sterilization. Communication of the scope or camera 26 with the screen 34 is conveniently provided through a fiber optic tube 35 via optic fibers as is well-known in the art. It is also envisioned that the camera means 26 could comprise a computer chip camera or similar camera means now in development.

By positioning the display screen 34 on the handle 21 of the laryngoscope 18 and enabling it to swivel, as best seen in FIG. 3, the intubator 12 can simultaneously view the area of the trachea opening 23 directly and on the screen 34 without substantial motion of the Professional Intubator's 12 eye 14. The Professional Intubator's 12 right hand 36 is free to move and manipulate the intubating instrument 29 to guide it into the patient's trachea 23, rather than the patient's esophagus 31. The scope or camera 26 remains steady on the relatively stationary blade 17 of the laryngoscope 18 and is held firmly by the Professional Intubator's 12 left hand 37, so the visual field 27 seen by the camera 26 does not bounce around with necessary movement of the intubating instrument 29. The display on the screen 34 clearly depicts the trachea opening 23 and related structures and the Professional Intubator 12 sees the intubating instrument 29 passing into the trachea opening 23 both directly with his or her straight line of sight and also on the display screen 34 positioned quite close thereto.

It will be understood by those skilled in the art that various deviations may be made in the shown preferred embodiment without departing from a main theme of invention set forth in claims which follow.

I claim:

1. A laryngoscope comprising:

a handle and a blade, with the blade having a proximal end connected to the handle and a distal end projecting laterally therefrom;

camera means mounted on the blade in the vicinity of the distal end for observing a visual field; and display means operatively connected to said camera means for displaying the visual field at a preselected location.

2. The laryngoscope as claimed in claim 1, further including lighting means for illuminating the visual field.

3. The laryngoscope as claimed in claim 2, further including power supply means for powering said camera means and said display means.

4. The laryngoscope as claimed in claim 3, wherein said power supply means are mounted in the handle.

5. The laryngoscope as claimed in claim 1, wherein said display means include a screen mounted on the handle and on which is displayed the visual field observed by the camera means.

6. The laryngoscope as claimed in claim 5, wherein the camera means are a videocamera.

7. The laryngoscope as claimed in claim 5, wherein said display means organized to be lightweight.

8. The laryngoscope as claimed in claim 1, wherein said camera means are spaced from the distal end of the blade, fiberoptic means providing said operative connection between the camera means and the display means.

9. The laryngoscope as claimed in claim 8, wherein said fiberoptic means include a plurality of optic fibers.

10. The laryngoscope as claimed in claim 8, wherein said fiberoptic means include a fiberoptic tube.

11. The laryngoscope as claimed in claim 5, wherein said camera means comprise a computer chip camera.

12. The laryngoscope as claimed in claim 11, wherein said display means are connected electrically to said computer chip camera.

13. The laryngoscope as claimed in claim 1, characterized further in that it is made of lightweight strong plastic and is organized to be portable and the power supply means comprises a battery, the display means mounted on the handle adjacent to a line of sight of an intubator directly viewing the visual field itself.

14. The laryngoscope as claimed in claim 13, wherein the display means are positionable to allow the Professional Intubator simultaneous viewing of the visual field directly and the visual field indirectly through the display means.

15. A laryngoscope for use with an intubating instrument in a procedure for intubating a trachea of a patient, the laryngoscope comprising:

a handle for a Professional Intubator to grasp in a first hand, a blade with a proximal end connected to the handle and a distal end extending laterally therefrom for insertion into a patient's mouth during the procedure to elevate and move to one side the patient's tongue steadily and constantly;

camera means mounted on the blade in the vicinity of the distal end of the blade for observing a visual field that includes the patient's trachea opening and other oral internal structures;

the camera means connected operatively to a portable lightweight display means arranged for the Professional Intubator to see the field of view on the display means, whereby the Professional Intubator's second hand is available to manipulate the intubating instrument without disturbing the camera means.

16. A method of intubating a trachea of a patient by an Professional Intubator using an intubating instrument and a laryngoscope, the method comprising steps as follows:

providing the laryngoscope with a handle and a blade, the blade having a proximal end connected to the handle and a distal end projecting laterally therefrom;

inserting the blade into the patient's mouth while grasping the laryngoscope by the handle using a first hand of the Professional Intubator for steadily and constantly lifting and move to one side the patient's tongue and exposing the patient's trachea opening and other oral internal structures to view;

providing illuminating means for illuminating the trachea opening and other oral internal structures;

providing camera means mounted on the blade in the vicinity of the distal end of the blade so that it observes a field of view that includes the patient's trachea opening and other oral internal structures;

having the camera means operatively connected to display means for viewing the field of view thereon;

inserting the intubating instrument into the mouth of a patient using a second hand of the Professional Intubator and manipulating the intubating instrument for insertion of a tube into the patient's trachea opening;

positioning the display means on the handle so that while the Professional Intubator inserts and manipulates the intubating instrument into the patient's trachea the Professional Intubator observes the trachea opening and other oral internal structures of the patient on the display means unaffected by the manipulating of the intubating instrument.

* * * * *